United States Patent

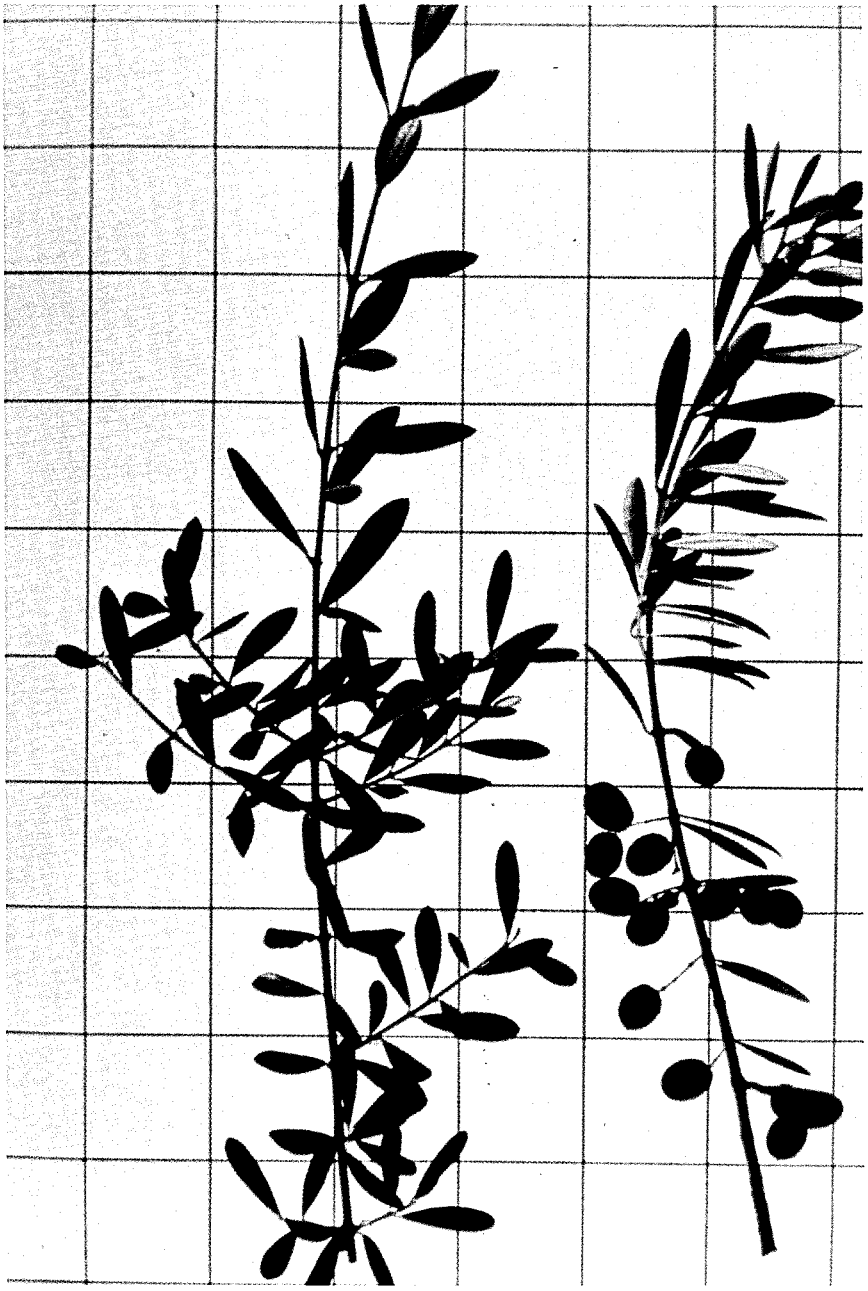

Plant Pat. 3,931

Patented July 6, 1976

3,931

WILT RESISTANT OLIVE TREE

Stephen Wilhelm and James E. Sagen, Berkeley, Calif., assignors to The Regents of the University of California, Berkeley, Calif.

Filed Oct. 29, 1974, Ser. No. 518,307

Int. Cl.[2] A01H 5/03

U.S. Cl. Plt.—33 1 Claim

The present invention relates to a new and distinct variety of Verticillium wilt resistant olive tree rootstock discovered after extensive search and to which may be grafted high yield commercial olive varieties.

The color photograph reproduction which accompanies this application identifies the rootstock tree of this invention but primarily illustrates typical branches with leaves and fruit free of Verticillium wilt disease through grown in soil bearing the Verticillium albo-atrum fungus.

The actual dimensions of the grid shown in the photograph are 5.0 cm. x 5.0 cm. The length of mature fruit as shown ranges from approximately 1.5 to 2.0 cm.

The rootstock is propagated vegetatively by cuttings to maintain its clonal integrity and is, therefore, asexually reproduced.

Vericillium wilt is a serious disease caused by the soil-borne fungus Verticillium albo-atrum (microsclerotial form) which enters the roots of olive trees of any age, from young trees to trees forty years old or more. The disease causes injury ranging from slight wilting and desiccation in twigs of a single branch to massive branch die-back and loss of the tree. Year by year the disease intensifies in olive groves and spreads. Some of the rapid devastation of established, old olive groves has been linked to adjacent disease infestations built up by the intensive growing of cotton. The culture of cotton is restricted by law to one variety which unfortunately is susceptible to the same wilt disease that affects olives.

The wilt resistant olive selection of this invention, which is called Berkeley 117, is the product of extensive testing since 1954 and which has been intensive since 1960 of olive seedling rootstocks of worldwide origin. More particularly, seed was obtained from agricultural experiment stations and botanical gardens in Argentina, Chile, France, Greece, Israel, Italy, Japan and Portugal, as well as from California sources. Large quantities of seed of 65 different accessions were obtained.

During the years 1963–1972, 6,000 seedling trees were inoculated with Verticillium and rated for resistance. This effort is believed to be one of the greatest efforts directed toward olive tree improvement conducted during the long history of the olive and with worthwhile results. It was found after working first at the University of California Deciduous Fruit Field Station at San Jose, Calif., a station devoted largely to Verticillium wilt research, that one year old seedling trees became infected rapidly with Verticillium and usually died within a few months after being inoculated. Trees were inoculated at the time they were removed from pots and planted in the soil. The inoculum consisted of a spore suspension in water of the fungus derived from laboratory cultures of known high virulence for olives.

Of the first groups inoculated comprising a total of approximately 1200 seedling trees, 93 survived and were healthy for four years. It was known from previous research that the Verticillium wilt fungus had the ability to invade the wood of olive trees and to spread into branches without causing any symptoms. Such an invaded tree, despite its own merits and vigorous growth, becomes a carrier of disease and unfit as a rootstock. Accordingly, to weed out carriers, portions of specifically tagged branches of each of the 93 surviving trees were brought to the laboratory at approximately one month intervals for two years and cultured for Verticillium. Because of the large diameter of the branches, the hardness of the wood and the many cultures required to obtain a meaningful result, a special medium selective for isolating the Verticillium fungus from olive was developed.

On the basis of the culturing, it was possible to rank the 93 symptomless trees into one of four different classes, namely, (1) continuously infected, (2) sporadically infected, (3) very occasionally infected and (4) free from detectable infection. Twenty-nine trees fell into the last class and all others, in which some infection was detected, were discarded. It is considered important to note that the 29 trees classed as free from infection were evaluated on the basis of repeated cultures of portions of one or a few branches only, rather than the entire tree. Thus, there still existed a possibility of missing infection if it occurred in some other part of the tree.

During the course of research, experiments were conducted on how to root cuttings of the resistant olives. A great variation in the readiness with which different trees rooted was found. Trees difficult to root were discarded. As the work progressed, blocks of rooted cuttings of the best "resistant" rootstock trees were given to Dr. Hudson T. Hartmann, Department of Pomology, University of California at Davis, California for studies on graft compatibility and long term evaluations on production and fruit quality. This study has been conducted at the San Joaquin Valley Agricultural Research and Extension Center at Parlier, Calif. and has involved several hundred trees. In 1970, testing was commenced of replicated clonal groups of the resistant rootstock trees derived from class 4 above identified. The testing took place in the University cotton wilt nursery on the Kleinhans Ranch, north of Visalia, Calif. on Road 112. On this ranch, Verticillium wilt is severe where ten acres have been devoted for several years to preliminary screening of cotton species, varieties and hybrids for resistance to Verticillium wilt. As before stated, cotton and olive are susceptible to the same strains of the Verticillium fungus. Olive selections, increased by cuttings, were planted directly in the heavily infested soil. Each selection was replicated three times, with generally 20–30 trees planted in each replication. Because of space limitations, only approximately 1,000 new trees could be planted each year.

Replicated groups of eleven clones of the 29 class 4 "resistant" trees were planted on the Kleinhans Ranch in 1970. During the period 1970–1973, a few clones died almost completely in all replications, a few showed a scattering of symptoms, and five clones have been almost totally free of the disease. Of these five clones, identified as 7–S2–8, 3–S5–117, 8–S14–79, 9–S14–110 and 10–S30–106, not more than one to three trees per clone developed symptoms during the first year. None developed symptoms after the first year. In 1972, trees of 7–S2–8 and 3–S5–117, together with some others which had shown some infection—a total of 84 trees—were grafted to the wilt susceptible Manzanillo variety. Grafts grew vigorously during 1973 and, except for control trees known to have been infected at the time of grafting, developed no symptoms. At the time of lopping of the rootstock tree above the graft, lopped portions were cultured for Verticillium and found to be negative except for susceptible trees grafted as controls. Grafted trees were dug and transplanted back into heavily infested soil to determine the effect of cutting roots and root damage on the resistance.

Rootstock tree 3–S5–117 was found to be the most resistant and mostly easily propagated, rooting up to 92% with bottom heat and intermittent mist. It has demonstrated high vigor as a rootstock and has been observed in the environments of Berekeley, San Jose, Tulare, and other southern areas of the San Joaquin Valley.

While this rootstock has shown a tendency to dwarf the Manzanillo variety, it does not dwarf the Ascalano, Sevillano or Mission varieties.

Rootstock tree 3–S5–117, which is now called Berkeley 117, is a single plant selection originating from seed of the European variety, Arbequina, grown for oil in several provinces in Spain and described there as a hardy, cold-tolerant, early-fruiting, medium-sized tree. As stated, the rootstock must be propagated vegetatively by cuttings for maintenance of its clonal integrity.

Definitive vegetative characteristics of the rootstock of this invention are as follows: mature leaves on branches bearing fruit are opposite in arrangement on the stem (which is characteristic of all species of the genus Olea), oblanceolate (as defined is Asa Gray, The Elements of Botany, Revised Edition, page 53, Figure 121) approximately 3.0 to 6.0 cm. in length, approximately 0.75 cm. to 1.0 cm. in width at their widest point. One hundred fruit allowed to mature without thinning on trees 10 years old displaced 255 cc. of water giving an average fruit volume of 2.55 cu. cm. The length of the mature fruit ranges from approximately 1.5 to 2.0 cm. and fruit size and volume are distinguishing characteristics of this new variety.

These vegetative characteristics are given with full realization that general habit of tree growth and leaf shape may vary with culture and age of the tree. In actual practice, the Verticillium wilt-resistant tree, Berkeley 117, will be below ground, extend up to the graft union, serving only as a rootstock for present commercial fruiting varieties. Its most definitive characteristic resides essentially in its disease resistance. In view of the great host range and diversity of strains of the Verticillium wilt fungus with differing capacities for pathogenicity, and in view of disease complexes, viz the presence of various root parasitic nematode species, it is not claimed that Berkeley 117 is resistant in all world localities or under all field circumstances.

It does appear, however, that Berkeley 117 is highly resistant, if not immune, to two different species of root knot nematodes known as *Meloidogyne Icognita* and *Meloidogyne javanica*.

We claim:

1. The new and distinct variety of olive tree (*Olea europaea* L.) useful as a rootstock to which may be grafted high yield commercial varieties, as herein described and illustrated, characterized particularly as to novelty by the small size and volume of its fruit, its high tolerance to the disease know as Verticillium wilt, its high vigor and ease of propagation.

No references cited.

ROBERT E. BAGWILL, Primary Examiner